United States Patent [19]
Pauza et al.

[11] Patent Number: 5,885,977
[45] Date of Patent: Mar. 23, 1999

[54] USE OF Δ5 ANDROSTENES IN THE TREATMENT OF HIV WASTING SYNDROME

[75] Inventors: C. David Pauza; Henry A. Lardy, both of Madison, Wis.

[73] Assignee: Humanetics Corporation, St. Louis Park, Minn.

[21] Appl. No.: 784,856

[22] Filed: Jan. 15, 1997

[51] Int. Cl.$^6$ .................................................. A61K 31/56
[52] U.S. Cl. .......................................... 514/171; 514/178
[58] Field of Search ..................................... 514/171, 178

[56] References Cited

U.S. PATENT DOCUMENTS

| | | | |
|---|---|---|---|
| 5,292,730 | 3/1994 | Landy | 514/171 |
| 5,506,223 | 4/1996 | Landy et al. | 514/178 |

OTHER PUBLICATIONS

Landy et al. 1995, 123 CA:83832e.
"Oxandrin"brochure, 1995.
Cat et al., "Treatment for HIV Wasting Syndrome," *The Annals of Pharmacotherapy*, vol. 28, No. 5, pp. 595–597, May 1994.
Coodley et al., "The HIV Wasting Syndrome: A Review," *Journal of Acquired Immune Deficiency Syndromes*, vol. 7, No. 7, pp. 681–694, 1994.
Grunfeld et al., "Pathophysiology of the AIDS Wasting Syndrome," *AIDS Clinical Review*, pp. 191–224, 1992.
Kotler, "Wasting Syndrome: Nutritional Support in HIV Infection," *AIDS Research and Human Retroviruses*, vol. 10, No. 8, pp. 931–934, Aug. 1994.
Nahlen et al., "Wasting Syndrome in the United States," *AIDS*, vol. 7, No. 2, pp. 183–188, 1993.
Weinroth et al., "Wasting Syndrome in AIDS: Pathophysiologic Mechanisms and Therapeutic Approaches," *Infectious Agents and Disease*, vol. 4, No. 2, pp. 76–94, 1995.
Zangerle et al., "Weight loss in HIV–1 infection is associated with immune activation," *AIDS*, vol. 7, No. 2, pp. 175–181, 1993.

*Primary Examiner*—Russell Travers
*Attorney, Agent, or Firm*—Michael S. Sherrill

[57] ABSTRACT

HIV-related weight loss, HIV-related cachexia and HIV-related wasting syndrome can be treated by administering therapeutic amounts of the steroid Δ5-androstene-3β-ol-7,17 dione and metabolizable precursors thereof, such as Δ5-androstene-3β-acetoxy-7,17 dione, which are readily metabolized in vivo to Δ5 androstene-3β-ol-7,17 dione. Such treatment can be prophylactic, modulatory, ameliorative or curative in nature.

27 Claims, 3 Drawing Sheets

USE OF Δ5 ANDROSTENES IN THE TREATMENT OF HIV WASTING SYNDROME

FIELD OF THE INVENTION

This invention broadly relates to treatment strategies for HIV-associated weight loss and the HIV wasting syndrome. More specifically, the invention relates to prophylactic, modulatory, ameliorative and curative drug therapies for HIV-related weight loss and HIV-related wasting.

BACKGROUND

An involuntary and progressive loss in body weight is a common symptom of HIV infection (hereinafter "HIV-related cachexia"). Such weight loss can be conveniently categorized as "chronic" when the weight loss occurs gradually over a period of about three months, and "acute" when the weight loss occurs rapidly (i.e., over a period of less than about three months) with an eventual recovery of the lost weight. As defined by the Centers for Disease Control (hereinafter "CDC"), when such weight loss amounts to greater than a ten percent (10%) loss in baseline body weight and is combined with either chronic diarrhea (i.e., at least two loose stools per day for more than thirty days) or chronic weakness and fever (i.e., weakness and/or fever which has been constant or intermittent for more than thirty days) in the absence of a secondary infection (i.e., lack of an infectious agent other than HIV which may account for any of the referenced symptoms), the weight loss is classified as HIV-related wasting syndrome (hereinafter "wasting syndrome"). It is noted that, based upon this definition of the wasting syndrome, all persons afflicted with the wasting syndrome suffer from HIV-related cachexia, but only a portion of those suffering from HIV-related cachexia are afflicted with the wasting syndrome.

In contrast to starvation-induced weight loss, HIV-related cachexia results in profound tissue depletion that does not respond readily to nutritional therapy.

It has been suggested by various researchers in the field that the wasting syndrome would best be characterized by the degree of involuntary depletion of lean body mass, predominately muscle protein, rather than simply body weight. However, this suggestion has not been widely accepted by the medical community and is still being debated.

The wasting syndrome is known to play a major role in the decreased quality of life of AIDS patients, and constitute a major cause of morbidity and mortality in patients infected with HIV. After years of ignoring the syndrome, the CDC officially recognized the wasting syndrome as an AIDS-defining illness in 1987. Despite the use of antiretroviral agents, improvements in therapy and prophylaxis against many of the major disease complications, the prevalence of the wasting syndrome is increasing.

Etiology

It is widely believed that HIV-related cachexia and the wasting syndrome are mediated by a combination of factors including hypermetabolism, metabolic derangement, decreased caloric intake, malabsorption, cytokine activity, endocrine dysfunction, and myopathy.

Various treatment regimens have been investigated, including enteral & parenteral alimentation, appetite stimulants, anabolic agents, cytokine modulators and fatty acid supplements, with limited success. Hence, the search continues for alternative treatments for HIV-related cachexia and the wasting syndrome.

SUMMARY OF THE INVENTION

The invention is directed to the prophylactic, modulatory, ameliorative and curative treatment of HIV-related weight loss, HIV-related cachexia and HIV-related wasting syndrome by administering the steroid Δ5-androstene-3β-ol-7,17 dione and precursors thereof which are readily metabolized in vivo to Δ5-androstene-3β-ol-7,17 dione.

DETAILED DESCRIPTION OF THE INVENTION INCLUDING A BEST MODE

HIV-related weight loss, HIV-related cachexia and HIV-related wasting syndrome can be treated by administering therapeutic amounts of the steroid Δ5-androstene-3β-ol-7,17 dione and 3β ester derivatives thereof, such as Δ5-androstene-3β-acetoxy-7,17 dione, which are readily metabolized in vivo to Δ5-androstene-3β-ol-7,17 dione. Such treatment can be prophylactic, modulatory, ameliorative or curative in nature.

The Steroid

The steroid Δ5-androstene-3β-ol-7,17 dione is a derivative of dehydroepiandrosterone (DHEA) which does not appreciably stimulate, increase or otherwise enhance the production of sex hormones. The steroid is commercially available from a number of sources including Steraloids, Inc. of Wilton, N.H. A number of procedures are available for synthesizing Δ5-androstene-3β-ol-7,17 dione from DHEA, with one such procedure described in U.S. Pat. No. 5,296,481.

Precursors of Δ5-androstene-3β-ol-7,17 dione may also be usefully employed in the treatment of HIV-related weight loss, HIV-related cachexia and HIV-related wasting syndrome. Such precursors are readily metabolized in vivo to the active Δ5-androstene-3β-ol-7,17 dione. One example of such a metabolizable precursor is the commercially available Δ5-androstene-3β-acetyl-7,17 dione. The 3β-acetyl group is hydrolyzed in vivo by esterases located in the blood and various tissue to produce the active Δ5-androstene-3β-ol-7,17 dione, and is believed to be less susceptible to oxidation during the manufacturing process than the hydroxy group found on the active Δ5-androstene-3β-ol-7,17 dione. Other metabolizable precursors include Δ5-androstene-3β, 17β-diol-7-one, Δ5-androstene-3β, 7α-diol-17-one, Δ5-androstene-3β, 7β-diol-17-one and the corresponding acetyl esters of these steroids.

Administration

Administration Route

The Δ5 Androstene-3-acetoxy-7,17-dione can be administered by virtually any of the commonly accepted practices for the administration of pharmaceutical preparations including specifically, but not exclusively, mucosal administration, oral consumption, ocular administration, subcutaneous injection, transdermal administration, etc.

Mucosal administration of the steroid includes such routes as buccal, endotracheal, nasal, pharyngeal, rectal, sublingual, vaginal, etc. For administration through the buccal/sublingual/pharyngeal/endotracheal mucosa, the steroid may be formulated as an emulsion, gum, lozenge, spray, tablet or an inclusion complex such as cyclodextrin inclusion complexes. Nasal administration is conveniently conducted through the use of a sniffing power or nasal spray. For rectal and vaginal administration the steroid may be formulated as a cream, douch, enema or suppository.

Oral consumption of the steroid may be effected by incorporating the steroid into a food or drink, or formulating the steroid into a chewable or swallowable tablet.

Ocular administration may be effected by incorporating the steroid into a solution or suspension adapted for ocular application such as drops or sprays.

Subcutaneous administration involves incorporating the steroid into a pharmaceutically acceptable and injectable carrier.

For transdermal administration, the steroid may be conveniently incorporated into a lipophilic carrier and formulated as a topical creme or adhesive patch.

Dose Rate

The range of dosages and dose rates effective for achieving the desired biological properties and characteristics may be determined in accordance with standard industry practices. These ranges can be expected to differ depending upon whether the desired response is the prophylactic, modulatory, ameliorative or curative treatment of HIV-related weight loss, HIV-related cachexia or HIV-related wasting.

EXPERIMENTAL

Experiment 1

(Preparation of Δ5 Androstene-3-acetoxy-7,17-dione)

Step One (Preparation of Δ5Androstene-3-acetoxy-17-one)

A suitable, three-necked, round-bottom flask equipped with an overhead stirrer, reflux condenser, mineral oil filled nitrogen bubbler and 110-volt temperature controller was charged with dehydroepiandrosterone (0.87 moles) purchased from Steraloids of Wilton, N.H., sodium acetate (1.04 moles), and glacial acetic acid (600 mL) to form a first mixture containing solid particles. The solid particles were broken and the first mixture stirred with the overhead stirrer to form a thick slurry.

Into the first mixture was added acetic anhydride (1.7 moles) to form a second mixture. The second mixture was heated to 65°±5° C. under constant agitation for about 18 hours. Upon completion of the reaction, as established by TLC, heat was removed from the reaction flask.

The fully reacted second mixture was diluted with water (1.5 L) to form a diluted second mixture. The diluted second mixture was stirred at 20°–25° C. for about 2 hours, after which a solid product was collected by vacuum filtration through a 17.5 cm Buchner funnel lined with Whatman #1 filter paper. The reaction flask and filter cake were rinsed with water (2×500 mL) and the filter cake air dried on the filter for 3 hours to form a dry crude solid product.

The crude solid product was transferred to a 4 liter Erlenmeyer flask, equipped with a large magnetic stirrer and a thermometer, and dispersed in ethanol (2.2 L) to form a third mixture. The third mixture was then placed on a stirring hot plate, the magnetic stirrer activated, and the third mixture heated to the boiling point (78° C.). A clear solution was obtained when the third mixture reached 65° C.

The clear solution was vacuum filtered through a 7.0 cm Buchner funnel lined with Whatman #1 filter paper and the filtrate directed into a 3 liter, three-necked, round-bottom flask equipped with an overhead stirrer and vacuum take off (nothing collected on the filter paper). The flask and filter paper were rinsed with hot (approximately 75° C.) fresh ethanol and the filtered rinse added to the filtrate. A thermometer was inserted into the flask and the filtrate heated under constant agitation until the filtrate reached 59° C. The filtrate was then cooled to room temperature, with crystals appearing at 49° C., and the crystal-containing filtrate stirred overnight.

The next morning a solid product was collected by vacuum filtration through a 17.5 cm Buchner funnel lined with Whatman #1 filter paper. The filter cake was rinsed with fresh ethanol (2×100 mL), air dried for 1 hour, and then dried in vacuo at 50° C. for 20 hours. The filtrate and wash liquor were collected in a suitable container for later processing. The process yielded 252.4 grams of solid Δ5 Androstene-3-acetoxy-17-one.

The combined mother/wash liquors were concentrated at 45° C. under a reduced pressure of 24 to 26 inches Hg vacuum to about 500 ML and allowed to stand overnight at room temperature. The next morning a second crop of solid product was collected by vacuum filtration through a 17.5 cm Buchner funnel lined with Whatman #1 filter paper. The resultant filter cake was rinsed with fresh ethanol (2×100 mL), air dried for 1 hour, and then dried in vacuo at 55° C. for 20 hours to yield an additional 24.9 grams of solid Δ5 Androstene-3-acetoxy-17-one. The first and second crops were combined to produce a total of 277.3 grams of Δ5 Androstene-3-acetoxy-17-one.

Theoretical yield=287.5 g

First crop yield=252.4 g (88%)

Second crop yield=24.9 g (9%)

Step Two (Preparation of Crude Δ5 Androstene-3-acetoxy-7,17-dione)

A suitable, three-necked, round-bottom flask equipped with an overhead stirrer, reflux condenser, mineral oil filled bubbler and a gas inlet tube connected to an oxygen cylinder, was charged with N-hydroxyphthalimide (0.15 moles) and 2-butanone (400 mL) to form a premix. The premix was heated to reflux (80° C.) under constant agitation and 0.15 moles of the Δ5 Androstene-3-acetoxy-17-one prepared in Step One added to form a first reaction mixture.

A steady stream of oxygen was into the flask from the oxygen cylinder and 2,2'-azobis (2-methylpropionitrile) (AIBN) (0.012 moles) added to the first reaction mixture to form an initiated first reaction mixture. The initiated first reaction mixture was refluxed for about 12 hours, with progression of the reaction monitored by TLC at t=2, 6, 8 and 10 hours, with additional AIBN (0.012 moles) added after each TLC measurement. The fully reacted first reaction mixture was then cooled slightly and solvent removed in vacuo to form a solid product.

The resulting solid product was suspended in methyl t-butyl ether (MtBE) (800 mL), the suspension heated to reflux (56° C.) for 30 minutes, and then filtered. The filtrate was cooled to room temperature, transferred to a 2 liter separatory funnel, washed with a saturated sodium bicarbonate solution (6×800 mL), and then washed with water (800 mL) to form an organic solids fraction. The organic solids fraction was concentrated in vacuo to near dryness and placed in a freezer (−5° C.) overnight. The next morning the frozen organic solids fraction was collected by filtration, washed with cold MtBE (100 mL), and dried overnight at room temperature under high vacuum (<1 mm Hg vacuum). The process yielded 27.13 grams of crude solid Δ5 Androstene-3-acetoxy-7,17-dione.

Theoretical yield=52.33 g

Actual yield=27.13 g (52%)

Step Three
(Preparation of Purified Δ5 Androstene-3-acetoxy-7,17-dione)

A 250 mL Erlenmeyer flask equipped with a magnetic stirrer was charged with 26.5 grams of the crude Δ5 Androstene-3-acetoxy-7,17-dione prepared in Step Two and 150 mL of ethanol to form a first suspension. The magnetic stirrer was activated and the suspension heated to the boiling point (78° C.) until the crude Δ5 Androstene-3-acetoxy-7,17-dione dissolved in the ethanol to form a first solution. The first solution was clarified by vacuum filtration. The flask and filter were rinsed with hot ethanol (25 mL) with the wash liquor passed through the filter and combined with the filtrate. The combined filtrate and wash liquor (hereinafter combined filtrate) were placed in a suitable flask.

A magnetic stir bar was added to the combined filtrate (which had solidified) and the combined filtrate reheated until the solids content was again dissolved in the solvent. The flask was removed from the heat, placed on a magnetic stir plate and the stirrer started. The heated solution was cooled to room temperature under constant agitation, with crystallization starting at approximately 50° C., and then placed in an ice bath for 30 minutes so as to form a white solid precipitate in the combined filtrate. The white solid precipitate was collected by vacuum filtration, washed with cold ethanol (30 mL), and dried overnight at room temperature under high vacuum (<1 mm Hg vacuum).). The process yielded 23.0 grams of purified solid Δ5 Androstene-3-acetoxy-7,17-dione.

Theoretical recovery=26.5 g

Actual recovery=23.0 g (87%)

Experiment 2a
(Treatment of SIV infected rhesus macaques (*Macaca mulatta*) with Δ5 Androstene-3-acetoxy-7,17-dione)

Animals and Virus

Two male rhesus macaques (hereinafter designated as animals 101 and 102) were selected from a colony which had been previously infected with SIV (SIVmac 251 biological isolate kindly provided by Dr. Ronald C. Desrosiers of the New England Primate Research Center) and enrolled in studies of virus transmission or pathogenesis. The animals were infected by intrarectal inoculation. Infection of both animals was confirmed by measuring SIV binding antibodies in peripheral blood plasma using commercially available HIV-2 ELISA assay kits purchased from Genetic Systems Inc. of Seattle, Wash.

Treatment with Steroid

Figure 1:
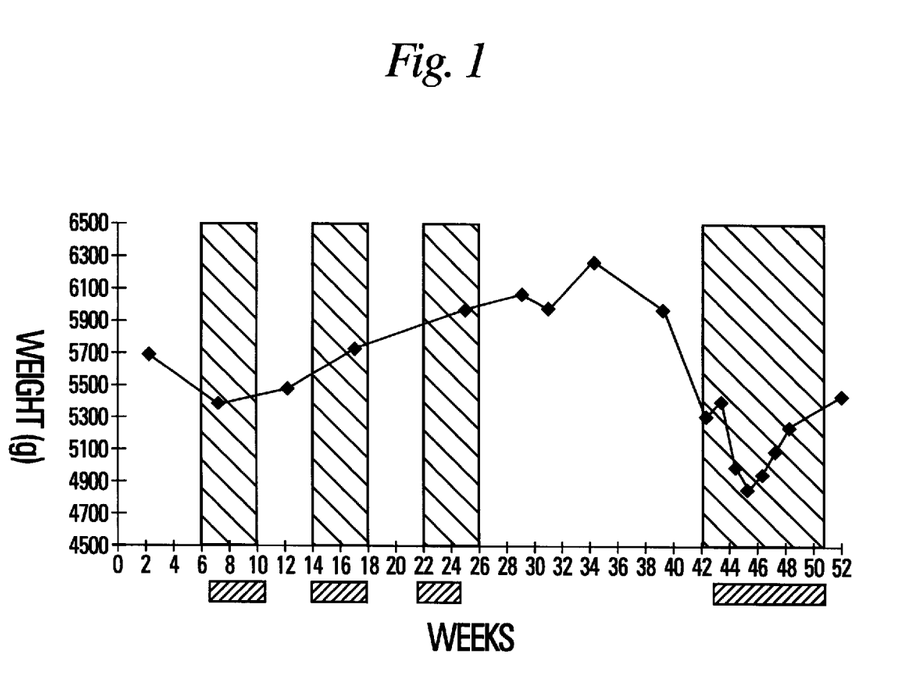
FIG. 1 is a graphical depiction of Experiment Two for animal 101.
Figure 2:
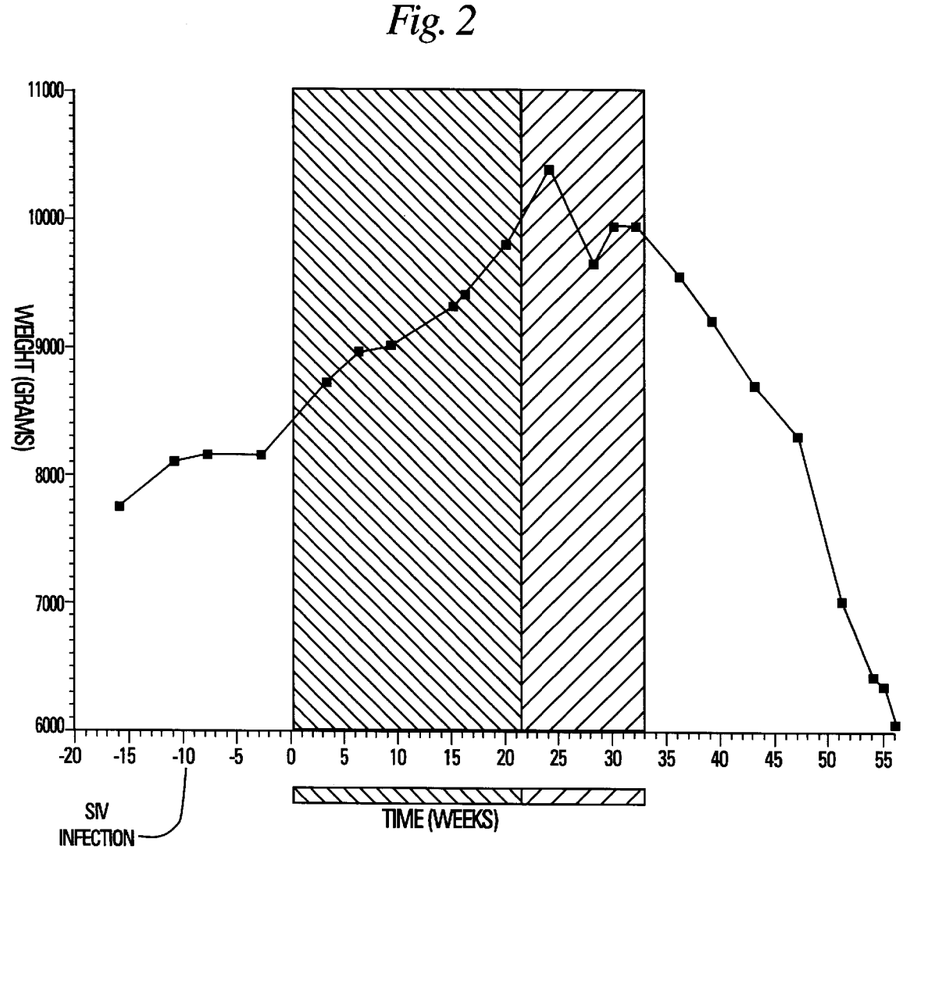
FIG. 2 is a graphical depiction of Experiment Two for animal 102.

Δ5 Androstene-3-acetoxy-7,17-dione was administered to each of the animals by incorporating the steroid into a peanut butter and honey sandwich fed to each of the animals at 7:00 a.m. on the days indicated in Tables One and Two. The animals were periodically weighed on the Monday of each week as indicated in Tables One and Two. The dosage, dose rate, weekly administration schedule and measured body weight of each animal are provided in Tables One and Two, and depicted graphically in FIGS. 1 and 2.

Conclusions

Both animals developed characteristic clinical manifestations of chronic SIV infection before treatment and when the steroid was withdrawn. This condition included persistent and generalized lymphadenopathy, weight loss and erythematosus rash. When on treatment, both animals exhibited signs of stabilization and improvement such as weight maintenance, weight gain, increased alertness, heighten appetite, loss of rash and enhanced activity level. This was especially true for animal 101, who lost more than 22% of body weight in less than three months when taken off the drug for an extended period of time and then regained a significant portion of that lost weight upon treatment with the steroid (weeks 71 through 91 depicted in Table One and FIG. 1).

Signs of intolerance (nausea, vomiting, fatigue, or lack of weight gain) and negative changes in blood chemistry parameters were not observed in either animal during the treatment period.

These initial experiments demonstrate that Δ5 Androstene-3-acetoxy-7,17-dione is effective for maintaining body weight, increasing body weight, and reversing the wasting syndrome in SIV infected rhesus primates.

TABLE ONE

ANIMAL 101

| WEEKS AFTER INFECTED | WEIGHT (GRAMS) | DOSE RATE (MG/DAY) | DAYS PER WEEK |
|---|---|---|---|
| 1 | | | |
| 2 | | | |
| 3 | | | |
| 4 | | | |
| 5 | | | |
| 6 | | | |
| 7 | | | |
| 8 | | | |
| 9 | | | |
| 10 | | | |
| 11 | | | |
| 12 | | | |
| 13 | | | |
| 14 | | | |
| 15 | | | |
| 16 | | | |
| 17 | | | |
| 18 | | | |
| 19 | | | |
| 20 | | | |
| 21 | | | |
| 22 | | | |
| 23 | | | |
| 24 | | | |
| 25 | | | |
| 26 | | | |
| 27 | | | |
| 28 | | | |
| 29 | | | |
| 30 | | | |
| 31 | | | |
| 32 | | | |
| 33 | | | |
| 34 | | | |
| 35 | | | |
| 36 | | | |
| 37 | | | |
| 38 | | | |
| 39 | | | |
| 40 | | | |
| 41 | 5700 | | |
| 42 | | | |
| 43 | | | |
| 44 | | | |
| 45 | | 500 | 5 |
| 46 | 5400 | 500 | 5 |
| 47 | | 500 | 5 |
| 48 | | 500 | 5 |
| 49 | | | |
| 50 | | | |
| 51 | 5500 | | |
| 52 | | | |
| 53 | | 500 | 5 |
| 54 | | 500 | 5 |
| 55 | | 500 | 5 |
| 56 | 5750 | 500 | 5 |
| 57 | | | |

TABLE ONE-continued

ANIMAL 101

| WEEKS AFTER INFECTED | WEIGHT (GRAMS) | DOSE RATE (MG/DAY) | DAYS PER WEEK |
|---|---|---|---|
| 58 | | | |
| 59 | | | |
| 60 | | | |
| 61 | | 500 | 5 |
| 62 | | 500 | 5 |
| 63 | | 500 | 5 |
| 64 | 6000 | 500 | 5 |
| 65 | | | |
| 66 | | | |
| 67 | | | |
| 68 | 6100 | | |
| 69 | | | |
| 70 | 6000 | | |
| 71 | | | |
| 72 | | | |
| 73 | 6300 | | |
| 74 | | | |
| 75 | | | |
| 76 | | | |
| 77 | | | |
| 78 | 6000 | | |
| 79 | | | |
| 80 | | | |
| 81 | 5350 | 500 | 7 |
| 82 | 5450 | 500 | 7 |
| 83 | 5050 | 500 | 7 |
| 84 | 4900 | 500 | 7 |
| 85 | 5000 | 500 | 7 |
| 86 | 5150 | 500 | 7 |
| 87 | 5300 | 500 | 7 |
| 88 | | 500 | 7 |
| 89 | | 500 | 7 |
| 90 | | | |
| 91 | 5500 | 500 | 7 |

TABLE TWO

ANIMAL 102

| WEEKS AFTER INFECTED | WEIGHT (GRAMS) | DOSE RATE (MG/DAY) | DAYS PER WEEK |
|---|---|---|---|
| −10 | | | |
| −9 | | | |
| −8 | | | |
| −7 | | | |
| −6 | 7750 | | |
| −5 | | | |
| −4 | | | |
| −3 | | | |
| −2 | | | |
| −1 | 8100 | | |
| 0 | | | |
| 1 | | | |
| 2 | 8150 | | |
| 3 | | | |
| 4 | | | |
| 5 | | | |
| 6 | | | |
| 7 | 8150 | | |
| 8 | | | |
| 9 | | | |
| 10 | | 500 | 5 |
| 11 | | 500 | 5 |
| 12 | | 500 | 5 |
| 13 | 8700 | 500 | 5 |
| 14 | | 500 | 5 |
| 15 | | 500 | 5 |
| 16 | 8950 | 500 | 5 |
| 17 | | 500 | 5 |
| 18 | | 500 | 5 |

TABLE TWO-continued

ANIMAL 102

| WEEKS AFTER INFECTED | WEIGHT (GRAMS) | DOSE RATE (MG/DAY) | DAYS PER WEEK |
|---|---|---|---|
| 19 | 9000 | 500 | 5 |
| 20 | | 500 | 5 |
| 21 | | 500 | 5 |
| 22 | | 500 | 5 |
| 23 | | 500 | 5 |
| 24 | | 500 | 5 |
| 25 | 9300 | 500 | 5 |
| 26 | 9400 | 500 | 5 |
| 27 | | 500 | 5 |
| 28 | | 500 | 5 |
| 29 | | 500 | 5 |
| 30 | 9800 | 500 | 5 |
| 31 | | 500 | 5 |
| 32 | | 100 | 5 |
| 33 | | 100 | 5 |
| 34 | 10400 | 100 | 5 |
| 35 | | 100 | 5 |
| 36 | | 100 | 5 |
| 37 | | 100 | 5 |
| 38 | 9650 | 100 | 5 |
| 39 | | 100 | 5 |
| 40 | 9950 | 100 | 5 |
| 41 | | 100 | 5 |
| 42 | 9950 | 100 | 5 |
| 43 | | | |
| 44 | | | |
| 45 | | | |
| 46 | 9550 | | |
| 47 | | | |
| 48 | | | |
| 49 | 9200 | | |
| 50 | | | |
| 51 | | | |
| 52 | | | |
| 53 | 8700 | | |
| 54 | | | |
| 55 | | | |
| 56 | | | |
| 57 | 8300 | | |
| 58 | | | |
| 59 | | | |
| 60 | | | |
| 61 | 7050 | | |
| 62 | | | |
| 63 | | | |
| 64 | 6450 | | |
| 65 | 6400 | | |
| 66 | 6100 | | |

Experiment 2b (Treatment of Additional SIV infected rhesus macaque (*Macaca mulatta*) with Δ5 Androstene-3-acetoxy-7,17-dione)

Animals and Virus

A male rhesus macaque (hereinafter designated as animal 201) was infected with SIV (SIVmac 251 biological isolate kindly provided by Dr. Ronald C. Desrosiers of the New England Primate Research Center). The animal was infected by intrarectal inoculation. Infection of the animal was confirmed by measuring SIV binding antibodies in peripheral blood plasma using commercially available HIV-2 ELISA assay kits purchased from Genetic Systems Inc. of Seattle, Wash.

Treatment with Steroid

Figure 3:
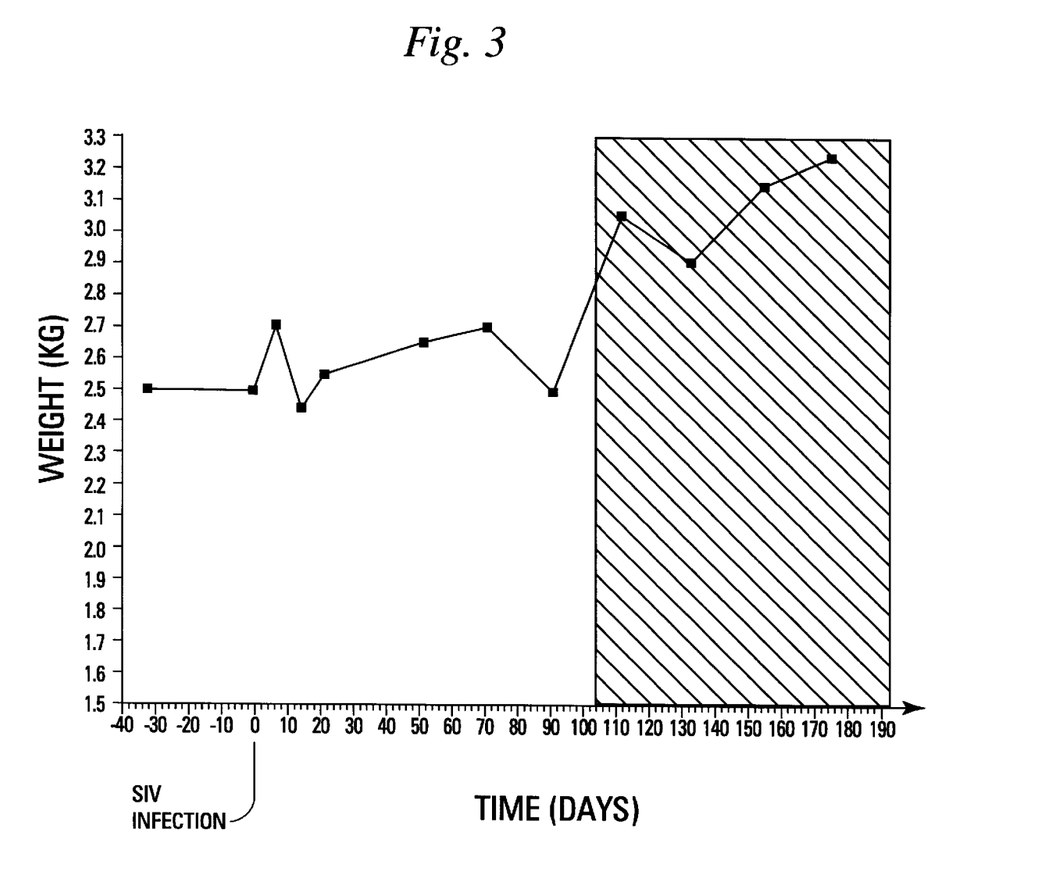
FIG. 3 is a graphical depiction of Experiment Two for animal 201.

Δ5 Androstene-3-acetoxy-7,17-dione was administered to the animal by incorporating the steroid into a peanut butter and honey sandwich fed to the animal around 7:00 a.m. on the days indicated in Table Three. The animal was periodically weighed on the Monday of each week as indicated in Table Three. The dosage, dose rate, weekly administration schedule and measured body weight of the animal is provided in Table Three and depicted graphically in FIG. 3.

It is noted that several other male rhesus macaques were initially involved in the study but had to be excluded from the study due either to (i) an inability of the animal to mount a meaningful immune response, resulting in necropsy of the animal before treatment could be commenced, or (ii) the diagnosis of a secondary infection (typically gingivitis) which materially contributed to the animals loss of weight (e.g., the animal repeatedly refused food, including the sandwich containing the steroid).

Conclusions

The animal developed characteristic clinical manifestations of chronic SIV infection before treatment. This condition included persistent and generalized lymphadenopathy, a leveling of weight gain and erythematosus rash. When on treatment, the animal improved quickly and exhibited weight gain, increased alertness, heighten appetite, loss of rash and an enhanced activity level.

Signs of intolerance (nausea, vomiting, fatigue, or lack of weight gain) and negative changes in blood chemistry parameters were not observed in the animal during the treatment period.

TABLE THREE

| DAYS AFTER INFECTED | ANIMAL 201 WEIGHT (GRAMS) | DOSE RATE (MG/DAY) |
|---|---|---|
| −40 | | |
| −39 | | |
| −38 | | |
| −37 | | |
| −36 | | |
| −35 | 2500 | |
| −34 | | |
| −33 | | |
| −32 | | |
| −31 | | |
| −30 | | |
| −29 | | |
| −28 | | |
| −27 | | |
| −26 | | |
| −25 | | |
| −24 | | |
| −23 | | |
| −22 | | |
| −21 | | |
| −20 | | |
| −19 | | |
| −18 | | |
| −17 | | |
| −16 | | |
| −15 | | |
| −14 | | |
| −13 | | |
| −12 | | |
| −11 | | |
| −10 | | |
| −9 | | |
| −8 | | |
| −7 | | |
| −6 | | |
| −5 | | |
| −4 | | |
| −3 | | |
| −2 | | |
| −1 | | |
| 0 | 2500 | |
| 1 | | |
| 2 | | |
| 3 | | |
| 4 | | |
| 5 | | |
| 6 | | |
| 7 | 2700 | |
| 8 | | |
| 9 | | |
| 10 | | |
| 11 | | |
| 12 | | |
| 13 | | |
| 14 | 2450 | |
| 15 | | |
| 16 | | |
| 17 | | |
| 18 | | |
| 19 | | |
| 20 | 2550 | |
| 21 | | |
| 22 | | |
| 23 | | |
| 24 | | |
| 25 | | |
| 26 | | |
| 27 | | |
| 28 | | |
| 29 | | |
| 30 | | |
| 31 | | |
| 32 | | |
| 33 | | |
| 34 | | |
| 35 | | |
| 36 | | |
| 37 | | |
| 38 | | |
| 39 | | |
| 40 | | |
| 41 | | |
| 42 | | |
| 43 | | |
| 44 | | |
| 45 | | |
| 46 | | |
| 47 | | |
| 48 | | |
| 49 | 2650 | |
| 50 | | |
| 51 | | |
| 52 | | |
| 53 | | |
| 54 | | |
| 55 | | |
| 56 | | |
| 57 | | |
| 58 | | |
| 59 | | |
| 60 | | |
| 61 | | |
| 62 | | |
| 63 | | |
| 64 | | |
| 65 | | |
| 66 | | |
| 67 | | |
| 68 | | |
| 69 | | |
| 70 | | |
| 71 | 2700 | |
| 72 | | |
| 73 | | |
| 74 | | |
| 75 | | |
| 76 | | |
| 77 | | |

TABLE THREE-continued

ANIMAL 201

| DAYS AFTER INFECTED | WEIGHT (GRAMS) | DOSE RATE (MG/DAY) |
|---|---|---|
| 78 | | |
| 79 | | |
| 80 | | |
| 81 | | |
| 82 | | |
| 83 | | |
| 84 | | |
| 85 | | |
| 86 | | |
| 87 | | |
| 88 | | |
| 89 | | |
| 90 | | |
| 91 | 2500 | |
| 92 | | |
| 93 | | |
| 94 | | |
| 95 | | |
| 96 | | |
| 97 | | |
| 98 | | |
| 99 | | |
| 100 | | |
| 101 | | |
| 102 | | 20 |
| 103 | | 20 |
| 104 | | 20 |
| 105 | | 20 |
| 106 | | 20 |
| 107 | | 20 |
| 108 | | 20 |
| 109 | | 20 |
| 110 | | 20 |
| 111 | | 20 |
| 112 | 3050 | 20 |
| 113 | | 20 |
| 114 | | 20 |
| 115 | | 20 |
| 116 | | 20 |
| 117 | | 20 |
| 118 | | 20 |
| 119 | | 20 |
| 120 | | 20 |
| 121 | | 20 |
| 122 | | 20 |
| 123 | | 20 |
| 124 | | 20 |
| 125 | | 20 |
| 126 | | 20 |
| 127 | | 20 |
| 128 | | 20 |
| 129 | | 20 |
| 130 | | 20 |
| 131 | | 20 |
| 132 | | 20 |
| 133 | 2900 | 20 |
| 134 | | 20 |
| 135 | | 20 |
| 136 | | 20 |
| 137 | | 20 |
| 138 | | 20 |
| 139 | | 20 |
| 140 | | 20 |
| 141 | | 20 |
| 142 | | 20 |
| 143 | | 20 |
| 144 | | 20 |
| 145 | | 20 |
| 146 | | 20 |
| 147 | | 20 |
| 148 | | 20 |
| 149 | | 20 |
| 150 | | 20 |
| 151 | | 20 |
| 152 | | 20 |
| 153 | | 20 |
| 154 | 3150 | 20 |
| 155 | | 20 |
| 156 | | 20 |
| 157 | | 20 |
| 158 | | 20 |
| 159 | | 20 |
| 160 | | 20 |
| 161 | | 20 |
| 162 | | 20 |
| 163 | | 20 |
| 164 | | 20 |
| 165 | | 20 |
| 166 | | 20 |
| 167 | | 20 |
| 168 | | 20 |
| 169 | | 20 |
| 170 | | 20 |
| 171 | | 20 |
| 172 | | 20 |
| 173 | | 20 |
| 174 | 3250 | 20 |
| 175 | | 20 |
| 176 | | 20 |
| 177 | | 20 |
| 178 | | 20 |
| 179 | | 20 |
| 180 | | 20 |
| 181 | | 20 |
| 182 | | 20 |
| 183 | | 20 |
| 184 | | 20 |
| 185 | | 20 |
| 186 | | 20 |
| 187 | | 20 |
| 188 | | 20 |
| 189 | | 20 |
| 190 | | 20 |
| 191 | | 20 |
| 192 | | 20 |

I claim:

1. A treatment method comprising treating an HIV infected patient in need of such treatment with an effective weight loss modulatory amount of a $\Delta 5$-androstene-3$\beta$-ol-7,17 dione.

2. The treatment method of claim 1 wherein the method of treating an HIV-infected patient comprises treating an HIV-infected human patient.

3. The treatment method of claim 2 wherein the method of treating an HIV infected human patient comprises treating a human AIDS patient.

4. The treatment method of claim 2 wherein the method of treating an HIV infected patient in need of such treatment comprises prophylactically treating an HIV infected patient susceptible to HIV-related cachexia.

5. The treatment method of claim 2 wherein the method of treating an HIV infected patient in need of such treatment comprises treating an HIV infected patient afflicted with HIV-related cachexia.

6. The treatment method of claim 2 wherein the method of treating an HIV infected patient in need of such treatment comprises treating an HIV infected patient diagnosed with HIV-related cachexia.

7. The treatment method of claim 3 wherein the method of treating an AIDS patient in need of such treatment comprises treating an AIDS patient afflicted with HIV-related cachexia.

8. The treatment method of claim 3 wherein the method of treating an AIDS patient in need of such treatment comprises treating an AIDS patient diagnosed with HIV-related cachexia.

9. The treatment method of claim 3 wherein the method of treating an AIDS patient in need of such treatment comprises treating an AIDS patient suffering from HIV-related wasting syndrome.

10. The treatment method of claim 3 wherein the method of treating an AIDS patient in need of such treatment comprises treating an AIDS patient diagnosed with HIV-related wasting syndrome.

11. A treatment method comprising administering an effective weight loss ameliorating amount of a $\Delta 5$-androstene-3$\Delta$-ol-7,17 dione to an HIV infected patient in need of such treatment.

12. A treatment method comprising administering a therapeutic dose of a steroid selected from $\Delta 5$-androstene-3$\beta$-ol-7,17 dione and metabolizable precursors thereof to an HIV infected human patient exhibiting HIV-related weight loss.

13. The treatment method of claim 11 wherein the method of administering $\Delta 5$-androstene-3-ol-7,17 dione to an HIV-infected patient comprises administering $\Delta 5$-androstene-3$\beta$-ol-7,17 dione to an HIV-infected human patient.

14. The treatment method of claim 13 wherein the method of administering $\Delta 5$-androstene-3$\beta$-ol-7,17 dione to an HIV infected human patient comprises administering $\Delta 5$-androstene-3$\beta$-ol-7,17 dione to a human AIDS patient.

15. The treatment method of claim 13 wherein the method of administering $\Delta 5$-androstene-3$\beta$-ol-7,17 dione to an HIV infected patient in need of such treatment comprises administering $\Delta 5$-androstene-3$\beta$-ol-7,17 dione to an HIV infected patient suffering from HIV-related cachexia.

16. The treatment method of claim 12 wherein the method of administering a steroid to an HIV infected patient exhibiting HIV-related weight loss comprises administering a steroid to an HIV infected patient diagnosed with HIV-related cachexia.

17. The treatment method of claim 14 wherein the method of administering $\Delta 5$-androstene-3$\beta$-ol-7,17 dione to an AIDS patient in need of such treatment comprises administering $\Delta 5$-androstene-3$\beta$-ol-7,17 dione to an AIDS patient afflicted with HIV-related cachexia.

18. The treatment method of claim 14 wherein the method of administering $\Delta 5$-androstene-3$\beta$-ol-7,17 dione to an AIDS patient in need of such treatment comprises administering $\Delta 5$-androstene-3$\beta$-ol-7,17 dione to an AIDS patient diagnosed with HIV-related cachexia.

19. The treatment method of claim 12 wherein the method of administering a steroid to an HIV infected patient exhibiting HIV-related weight loss comprises administering a steroid to an AIDS patient suffering from HIV-related wasting syndrome.

20. The treatment method of claim 13 wherein the method of administering $\Delta 5$-androstene-3$\beta$-ol-7,17 dione to an AIDS patient in need of such treatment comprises $\Delta 5$-androstene-3$\beta$-ol-7,17 dione to an AIDS patient diagnosed with HIV-related wasting syndrome.

21. A treatment method comprising administering an effective HIV-related cachexia preventative amount of a $\Delta 5$-androstene-3$\beta$-ol-7,17 dione to an HIV infected patient susceptible to HIV-related cachexia.

22. The treatment method of claim 21 wherein the method of administering $\Delta 5$-androstene-3$\beta$-ol-7,17 dione to an HIV-infected patient susceptible to HIV-related cachexia comprises administering $\Delta 5$-androstene-3$\beta$-ol-7,17 dione to an HIV-infected human patient susceptible to HIV-related cachexia.

23. The treatment method of claim 22 wherein the method of administering $\Delta 5$-androstene-3$\beta$-ol-7,17 dione to an HIV infected human patient susceptible to HIV-related cachexia comprises administering $\Delta 5$-androstene-3$\beta$-ol-7,17 dione to a human AIDS patient susceptible to HIV-related cachexia.

24. A treatment method comprising treating an HIV infected patient afflicted with HIV-related cachexia with an effective curative amount of a steroid selected from $\Delta 5$-androstene-3$\beta$-ol-7,17 dione and metabolization precursors thereof.

25. The treatment method of claim 24 wherein the method of treating an HIV-infected patient afflicted with HIV-related cachexia comprising treating an HIV-infected human patient afflicted with HIV-related cachexia.

26. The treatment method of claim 25 wherein the method of treating an HIV infected human patient afflicted with HIV-related cachexia comprising treating a human AIDS patient afflicted with HIV-related cachexia.

27. The treatment method of claim 25 wherein the method of treating an HIV infected human patient afflicted with HIV-related cachexia comprising treating a human AIDS patient diagnosed with HIV-related wasting syndrome.

* * * * *